United States Patent [19]

Manning et al.

[11] 4,367,225
[45] Jan. 4, 1983

[54] NOVEL ANTAGONISTS OF THE ANTIDIURETIC AND/OR VASOPRESSOR ACTION OF ARGININE VASOPRESSIN

[75] Inventors: Maurice Manning, Toledo, Ohio; Wilbur H. Sawyer, Scarsdale, N.Y.

[73] Assignees: The Medical College of Ohio, Toledo, Ohio; The Trustees of Columbia University, New York, N.Y.

[21] Appl. No.: 247,008

[22] Filed: Mar. 24, 1981

[51] Int. Cl.³ .................. A61K 37/00; C07C 103/52
[52] U.S. Cl. ............................ 424/177; 260/112.5 R
[58] Field of Search ................. 424/177; 260/112.5 R

[56] References Cited

U.S. PATENT DOCUMENTS

| | | | |
|---|---|---|---|
| 3,371,080 | 2/1968 | Boissonnas et al. | 260/112.5 R |
| 3,415,805 | 12/1968 | Siedel et al. | 260/112.5 R |
| 3,418,307 | 12/1968 | Boissonnas et al. | 260/112.5 R |
| 3,454,549 | 7/1969 | Boissonnas et al. | 260/112.5 R |
| 3,497,491 | 2/1970 | Zavral | 260/112.5 R |
| 3,691,147 | 9/1972 | Manning | 260/112.5 R |
| 3,700,652 | 10/1972 | Manning | 260/112.5 R |
| 3,752,299 | 8/1973 | Jost et al. | 260/112.5 R |
| 4,148,787 | 4/1979 | Mulder et al. | 260/112.5 R |

OTHER PUBLICATIONS

Nestor et al., 18 J. Med. Chem. 1022 (1975).
Larsson, et al., 21 J. Med. Chem. 352 (1978).
Lowbridge, et al., 21 J. Med. Chem. 313 (1978).
Chan, et al., 161 Science 280 (1968).
Chan, et al., 174 J. Pharmacol. Exp. Ther. 541 (1970).
Chan, et al., 196 J. Pharmacol Exp. Ther. 746 (1976).
Dyckes, et al., 17 J. Med. Chem. 250 (1974).
Manning et al., 20 J. Med. Chem., 1228 (1977).
Bankowski, et al., 21 J. Med. Chem. 850 (1978).
Kruszynski et al., 23 J. Med. Chem. 364 (1980).

*Primary Examiner*—Delbert R. Phillips
*Attorney, Agent, or Firm*—Emch, Schaffer & Schaub

[57] ABSTRACT

Compounds acting as antagonists of the antidiuretic activity of arginine vasopressin are those of the formula

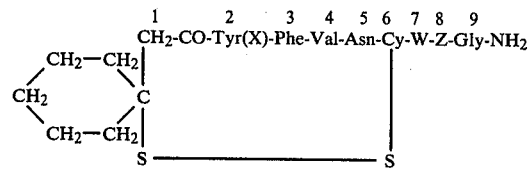

wherein X is methyl, ethyl, n-propyl, isopropyl or butyl; Tyr is D- or L-; W is Pro or $\Delta^3$-Pro; and Z is L- or D- Arg. Related compounds in which X is H, methyl or ethyl; W is Pro and Val at the 4-position is replaced by Gln- have antivasopressor activity against arginine vasopressin. Compounds wherein D-Tyr is unetherified (X is H), W- is Pro and Z- is D- or L-Arg also act as antagonists of the antidiuretic activity of arginine vasopressin.

17 Claims, 2 Drawing Figures

NOVEL ANTAGONISTS OF THE ANTIDIURETIC AND/OR VASOPRESSOR ACTION OF ARGININE VASOPRESSIN

The invention described herein was made in the course of work under a grant or award from the Department of Health and Human Services.

BACKGROUND OF THE INVENTION

This invention relates to novel peptides which antagonize the antidiuretic and/or vasopressor action of arginine vasopressin in vivo.

Prior Art Statement

Attempts to develop clinically useful synthetic antagonists of in vivo antidiuretic and/or vasopressor responses to arginine vasopressin, the antidiuretic hormone (ADH), have led to the synthesis and pharmacological evaluation of hundreds of analogs of the neurohypophysial peptides, oxytocin and vasopressin.

Analogs which can effectively antagonize in vivo vasopressor responses to ADH have been reported by Dyckes et al., *J. Med. Chem.*, vol. 17 (1974) at 250; Manning et al., *J. Med. Chem.*, vol. 20 (1977) at 1228; Bankowski et al., *J. Med. Chem.*, vol. 21 (1978) at 850; Kruszynski et al., *J. Med. Chem.*, vol. 23 (1980) at 364 and Lowbridge et al., *J. Med. Chem.*, vol. 21 (1978) at 313, herein incorporated by reference.

Kruszynski et al. reported that [1-($\beta$-mercapto-$\beta$,$\beta$-cyclopentamethylenepropionic acid), 2-(O-methyl)-tyrosine]arginine vasopressin and (1-$\beta$-mercapto-$\beta$,$\beta$-cyclopentamethylenepropionic acid]-arginine vasopressin are potent vasopressor antagonists, which also have very low antidiuretic potency.

Manning et al. (1977) described the synthesis of [1-deaminopenicillamine, 4-valine, 8-D-arginine] vasopressin and Lowbridge et al. the synthesis of [1-($\beta$-mercapto-$\beta$,$\beta$-cyclopentamethylenepropionic acid), 4-valine, 8-D-arginine] vasopressin. Both of these compounds have weak antidiuretic activity and are potent antagonists of the vasopressor response to AVP.

Analogs of vasopressin or oxytocin which antagonize antidiuretic responses to ADH have been reported by Chan et al., *Science*, vol. 161 (1968) at 280 and *J. Pharmacol. Exp. Ther.*, vol. 174 (1970) at 541 and vol. 196 (1976) at 746; Nestor et al., *J. Med. Chem.*, vol. 18 (1975) at 1022 and Larsson et al., *J. Med. Chem.*, vol. 21, (1978) at 352, herein incorporated by reference. None of the compounds reported has been pharmacologically or clinically useful as an antidiuretic antagonist.

Synthetic vasopressins have been disclosed in the following U.S. Pat. Nos.: 3,371,080 Boissonnas et al., 3,415,805 Siedel et al. 3,418,307 Boissonnas et al. 3,454,549 Boissonnas et al. 3,497,491 Zaoral 4,148,787 Mulder et al.

Of these references, Boissonnas et al., 3,371,080 discloses that 2-phenylalanine-8-ornithine vasopressin has a vasoconstrictive action equal to that of natural vasopressins but low antidiuretic activity. The remaining references disclose synthetic vasopressins having high or relatively specific antidiuretic activity.

Synthetic modifications of oxytocin are disclosed by Manning in U.S. Pat. Nos. 3,691,147 and 3,700,652.

It is therefore apparent that there is a continuing need for the development of pharmacologically and clinically effective antagonists of the antidiuretic action of arginine vasopressin.

OBJECT OF THE INVENTION

It is the object of the invention to provide antagonists to the antidiuretic action of ADH, which are effective in vivo. It is a further object to provide antagonists of the vasopressor action of ADH, which have low antidiuretic activity.

SUMMARY OF THE INVENTION

This invention relates to novel antagonists of the antidiuretic action of ADH, which are compounds of the formula wherein X is methyl, ethyl, n-propyl, isopropyl or butyl; Tyr is D- or L-; W is Pro or $\Delta^3$-Pro and Z is L- or D- Arg.

This invention further relates to a method for antagonizing the in vivo response to ADH, comprising administering to an animal being treated an amount of one of the foregoing compounds, in admixture with a physiologically and pharmaceutically acceptable carrier, effective to antagonize the antidiuretic response to ADH.

In another aspect, this invention relates to antagonists of the vasopressor action of ADH, the compounds being of the formula wherein X is H, methyl or ethyl and Z is L- or D- Arg. These compounds can be used in vivo for antagonizing a vasopressor response to a vasopressor hormone in an animal being treated.

DETAILED DESCRIPTION

Compounds provided in accordance with the invention are derivatives of arginine vasopressin (AVP). Amino acids are in the L- form unless otherwise indicated. The correlation between full names and abbreviations is: dAVP, 1-deamino-arginine vasopressin; dPAVP, [1-deaminopenicillamine] arginine vasopressin; d(CH$_2$)$_5$AVP, [1-($\beta$-mercapto-$\beta$,$\beta$-cyclopentamethylenepropionic acid)]-arginine vasopressin; dVDAVP, 1-deamino[4-valine, 8-D-arginine] vasopressin; dPVDAVP, [1-deaminopenicillamine, 4-valine, 8-D-arginine] vasopressin; d(CH$_2$)$_5$VDAVP, [1-($\beta$-mercapto-$\beta,\beta$-cyclopentamethylenepropionic acid), 4-valine, 8-D-arginine] vasopressin; dTyr(Me)AVP, 1-deamino[2-(O-methyl)-tyrosine] arginine vasopressin; dPTyr(Me)AVP [1-deaminopenicillamine, 2-(O-methyl)tyrosine] arginine vasopressin; d(CH$_2$)$_5$Tyr(me)VDAVP, [1-($\beta$-mercapto-$\beta,\beta$-cyclopentamethylenepropionic acid), 2-O-methyltyrosine, 4-valine, 8-D-arginine] vasopressin; d(CH$_2$)$_5$Tyr(Et)VDAVP, [1-($\beta$-mercapto-$\beta,\beta$-cyclopentamethylenepropionic acid), 2-O-ethyltyrosine, 4-valine, 8-D-arginine] vasopressin, d(CH$_2$)$_5$Tyr(Me)VAVP, [1-($\beta$-mercapto-$\beta,\beta$-cyclopentamethylenepropionic acid), 2-(O-methyl)-tyrosine, 4-valine] arginine vasopressin; d(CH$_2$)$_5$Tyr(Et)VAVP, [1-($\beta$-mercapto-$\beta,\beta$-cyclopentamethylenepropionic acid), 2-O-ethyltyrosine, 4-valine] arginine vasopressin; d(CH$_2$)$_5$Tyr(i-Pr)VDAVP, [1-($\beta$-mercapto-$\beta,\beta$-cyclopentamethylenepropionic acid), 2-(O-isopropyl)tyrosine, 4-valine, 8-D-arginine] vasopressin; d(CH$_2$)$_5$Tyr(n-Pr)-VDAVP, [1-($\beta$-mercapto-$\beta,\beta$-cyclopentamethylenepropionic acid), 2-(O-n-propyl)-tyrosine, 4-valine, 8-D-arginine] vasopressin; d(CH$_2$)$_5$Tyr(i-Pr)VAVP, [1-($\beta$-mercapto-$\beta,\beta$-cyclopentamethylenepropionic acid), 2-(O-isopropyl)-tyrosine, 4-valine] arginine vasopressin; d(CH$_2$)$_5$Tyr(n-Pr)VAVP, [1-($\beta$-mercapto-$\beta,\beta$-cyclopentamethylenepropionic acid), 2-(O-n-propyl)tyrosine, 4-valine] arginine vasopressin; and d(CH$_2$)$_5$Tyr(Et)V $\Delta^3$-Pro AVP, [1-($\beta$-mercapto-$\beta,\beta$-cyclopentamethylenepropionic acid), 2-(O-ethyl)tyrosine, 4-valine, 7-(3, 4-dehydroproline)] arginine vasopressin.

The active peptides were synthesized by solid phase synthesis as described by Bankowski et al. (1978), supra; Merrifield, *J. Am. Chem. Soc.*, vol. 85 (1963) at 2149 and *Biochemistry*, vol. 3 (1964) at 1385; Manning, *J. Am. Chem. Soc.*, vol. 90 (1968) at 1348; Manning et al., *J. Med. Chem.*, vol. 19 (1976) at 376; Lowbridge et al., *J. Med. Chem.*, vol. 20 (1977) at 1173; Manning et al., *J. Med. Chem.*, vol. 16 (1973) at 975 or Kruszynski et al. (1980), supra.

Peptides containing $\Delta^3$-Pro in the 7-position were also prepared in this fashion. Incorporation of $\Delta^3$-Pro into peptides has been described by Felix et al., *J. Peptide Protein Res.*, vol. 10 (1977) at 299 and Botos et al., *J. Med. Chem.*, vol 22 (1979) at 926.

Initial attempts to design an antagonist of the antidiuretic response to arginine vasopressin (AVP) included synthesis of [1-deaminopenicillamine, 4-valine, 8-D-arginine] vasopressin (dPVDAVP) by Manning et al. (1977), supra, and of [1-($\beta$-mercapto-$\beta,\beta$-cyclopentamethylenepropionic acid), 4-valine, 8-D-arginine] vasopressin (d(CH$_2$)$_5$VDAVP), Lowbridge (1978), supra. These analogs were designed by replacing the two hydrogens on the $\beta$-carbon at the 1-position of the highly active and selective antidiuretic peptide 1-deamino[4-valine, 8-D-arginine] vasopressin (dVDAVP), Manning et al., *J. Med. Chem.*, vol. 16 (1973) at 975, by two methyl groups and a cyclopentamethylene group, respectively. These substituents had previously been shown to convert the highly potent oxytocic agonist 1-deamino-oxytocin (dOT) into potent antagonists of the oxytocic response to oxytocin, specifically, [1-deaminopenicillamine] oxytocin (dPOT) and [1-($\beta$-mercapto-$\beta,\beta$-cyclopentamethylenepropionic acid)] oxytocin (d(CH$_2$)$_5$OT). See, Hope et al., *J. Biol. Chem.*, vol. 237 (1962) at 1563, Schulz et al., *J. Med. Chem.*, vol. 9 (1966) at 647 and Nestor et al., *J. Med. Chem.*, vol. 18 (1975) at 284.

Surprisingly, neither dPVDAVP nor d(CH$_2$)$_5$VDAVP was an antagonist of the antidiuretic response to AVP although possessing 0.1 and only 0.0001 the antidiuretic activity of dVDAVP, respectively. Each, however, was a potent antagonist of the vasopressor response to AVP, expressed as pA$_2$. pA$_2$ represents the negative logarithm to the base 10 of the average molar concentrations of antagonist which will reduce the specific biological response to 2x units of an agonist to the level of response to x units of the agonist. dPVDAVP and d(CH$_2$)$_5$VDAVP had antivasopressor pA$_2$ values of 7.82 and 7.68, respectively.

The discovery of these two vasopressor antagonists dPVDAVP and d(CH$_2$)$_5$VDAVP led to exploration of the effects of $\beta,\beta$-dimethyl and $\beta,\beta$-cyclopentamethylene substitutions at the 1-position in other analogs of AVP, particularly in combination with the substitution of O-methyltyrosine at the 2-position of the highly active antidiuretic and vasopressor agonist 1-deaminoarginine vasopressin (dAVP) in hopes of obtaining an antivasopressor peptide even more potent and selective than dPVDAVP or d(CH$_2$)$_5$VDAVP. See, Huguenin et al., *Helv. Chem. Acta.*, vol. 49 (1966) at 695; Manning et al., *J. Med. Chem.*, vol. 19 (1976) at 842 and Law et al., *J. Am. Chem. Soc.*, vol. 82 (1960) at 4579.

It was surprisingly found by Bankowski et al. (1978), supra, that of [1-deaminopenicillamine]-arginine vasopressin (dPAVP) and [1-deaminopenicillamine, 2-(O-methyl)tyrosine] arginine vasopressin (dPTyr(Me)-AVP), dPAVP was less potent than either dPVDAVP or d(CH$_2$)$_5$VDAVP but dPTyr(Me)AVP had an antivasopressor pA$_2$ of 7.96 and was the most potent antivasopressor peptide then known.

The effect on antivasopressor potency of combining the $\beta,\beta$-cyclopentamethylene and O-methyltyrosine substitutions in dAVP was developed in accordance with this invention to provide [1-($\beta$-mercapto-$\beta,\beta$-cyclopentamethylenepropionic acid), 2-(O-methyl)-tyrosine-arginine vasopressin (d(CH$_2$)$_5$Tyr(Me)AVP) of the structure This compound had very high antivasopressor potency and very weak antidiuretic activity, as did the unmethylated 2-tyrosine derivative, d(CH$_2$)$_5$AVP.

The compounds of this invention which have activity as antagonists of the antidiuretic activity of arginine vasopressin belong to the 4-valine-8-arginine vasopressin series and are of Formula I wherein Tyr is D- or L- and X and Z are:

| X | Z |
|---|---|
| Me | D-Arg |
| Et | D-Arg |
| Me | L-Arg |
| Et | L-Arg |
| i-Pr | D-Arg |
| n-Pr | D-Arg |
| i-Pr | L-Arg |
| n-Pr | L-Arg |
| Bu | L- or D- Arg |

Compounds of Formula II are as above, wherein Pro at the 7-position is replaced by $\Delta^3$-Pro.

The compounds of Formula I are related to a previously-reported antagonist of vasopressor responses to ADH, [1-(β-mercapto-β,β-cyclopentamethylenepropionic acid), 4-valine, 8-D-arginine] vasopressin d(CH$_2$)$_5$VDAVP, Lowbridge et al. (1978). Although not an antagonist of antidiuretic responses to ADH in vivo, this analog was a competitive antagonist of the activation of renal medullary adenylate cyclase by ADH in vitro, Butlen et al., *Mol. Pharmacol.*, vol. 14 (1978) at 1006. The work of Larsson et al. (1978), supra, also indicated the feasibility of making O-alkyl-tyrosine substitutions to convert this type of peptide into an antagonist of the antidiuretic response in vivo.

Compounds of Formula II contain a $\Delta^3$-Pro$^7$ unit thought by Botos et al., supra, to contribute to high antidiuretic activity of certain AVP analogues.

As shown by intraperitoneal administration of these compounds of the invention to normally-hydrated conscious rats, (O-ethyl)-tryrosine substitution at the 2-position in compounds of Formula I is more effective than (O-methyl)tyrosine substitution. The (O-propyl)-tyrosine compounds of Formula I also have impressive anti-ADH activity. However a 2-(O-Et)-tyrosine compound of Formula II is the most effective anti-ADH compound evaluated to present. The 8-L-arginine analogs are more potent than the corresponding 8-D-arginine analogs.

It appears that higher doses of d(CH$_2$)$_5$Tyr(Et)-VAVP almost completely block the antidiuretic action of endogenous ADH. For example, the 30 μg/kg dose of d(CH$_2$)$_5$Tyr(Et)VAVP raised urine flow to a mean of 27 ml/kg per hr during the second hour after injection. Spontaneous urine flow in female rats homozygous for the Brattleboro strain that secrete no ADH at all averages 32 ml/kg per hr, Sawyer, et al., *Endocrinology*, vol. 95 (1974) at 140.

The importance of minor structural modifications is indicated by findings that corresponding β,β-diethyl and β,β-dimethyl analogs of d(CH$_2$)$_5$Tyr(Et)VAVP do not exert detectable antagonistic activity in the intravenous rat antidiuretic assay. The presence of the 4-valine also contributes to antagonistic activity; Substitution of a 4-glutamine unit in d(CH$_2$)$_5$Tyr(Et)VAVP results in loss of antagonistic activity.

Compounds of the invention having Gln in the 4-position, which antagonize the vasopressor response to AVP, are useful in pharmacological studies on the role of AVP in regulating blood pressure under normal and pathophysiological conditions. Clinical applications include use as diagnostic and therapeutic antihypertensive agents. For therapeutic purposes, these compounds will be used in the same fashion as the known antihypertensive drug Captopril, D. B. Case et al., "Progress in Cardiovascular Diseases," vol. 21 (1978) at 195.

The compounds of Formulas I and II are very effective antagonists of the antidiuretic response to ADH. They can therefore be used in pharmacological studies on the contribution of ADH to a variety of pathological states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et al., *Am. J. Med.*, vol. 42 (1967) at 790.

The compounds of this invention can be employed in mixture with conventional excipients, i.e., physiologically and pharmaceutically acceptable organic or inorganic carriers suitable for parenteral or enteral application, which do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral or intranasal application, solutions, preferably oily or aqueous solutions, as well as suspensions, emulsions, or implants, including suppositories, are particularly suitable. Ampoules are convenient unit dosages.

For enteral application, particularly suitable are tablets, dragees, or capsules, having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The compounds of this invention are generally administered to animals, including but not limited to mammals, e.g., livestock, household pets, humans, cattle, cats and dogs. A diuretically effective daily dosage of the active compounds can be administered parenterally in a single dosage or as divided dosages throughout the day.

Parenteral or intranasal administration is preferred, the compounds of Formulas I and II of this invention being particularly valuable in the treatment of humans afflicted with water retention of any etiology. In this regard, they can be administered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organism being treated. Optimal application rates under a given set of conditions can be ascertained by those skilled in the art of using conventional dosage determination tests in view of the above guidelines.

DESCRIPTION OF PREFERRED EMBODIMENT

Preferred antidiuretic antagonists of the invention are [1-($\beta$-mercapto-$\beta$,$\beta$-cyclopentamethylenepropionic acid), 2-(O-ethyl)tyrosine, 4-valine]-arginine vasopressin, most preferably the 8-L-arginine compound. Also preferred is a corresponding $\Delta^3$-Pro$^7$ compound.

Without further elaboration, it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv. Chim. Acta*, vol. 56 (1973) at 1476 with Boc-Gly until 0.47 mmol/g and ~0.64 mmol/g were incorporated. Amino acid derivatives including Boc-Tyr(Me) ($R_f$(A) 0.7; $R_f$(B) 0.8) were supplied by Bachem Inc., or synthesized.

Triethylamine (TEA) and N-methylmorpholine (NMM) were distilled from ninhydrin.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were of analytical grade.

Thin layer chromatography (TLC) done on silica gel plates (0.25 mm, Brinkmann Silplate) using the following solvent systems: A. cyclohexane-chloroform-acetic acid (2:8:1 v/v); B. propan-1-ol-ammonia (34%) (2:1 v/v); C. ethanol (95%)-ammonia (34%) (3:1 v/v); D. chloroform-methanol (7:3 v/v); E. butan-1-ol-acetic acid-water (4:1:5 v/v, upper phase); F. butan-1-ol-acetic acid-water-pyridine (15:3:3:10 v/v). The applied loadings were 10–50 $\mu$g. The minimum length of the chromatograms was 10 cm. Chloroplatinate reagent and iodine vapor were used for development of the chromatograms.

Amino acid analysis of the peptides was done by the method of Spackman et al., *Anal. Chem.*, vol. 30 (1958) at 1190, in which peptide samples weighing about 0.5 mg were hydrolyzed with constant boiling hydrochloric acid (400 $\mu$l) in evacuated and sealed ampules for 18 h at 120° C. The analyses were performed using a Beckman Automatic Amino Acid Analyzer, Model 121. Molar ratios were referred to Gly=1.00. Elemental analyses were performed by Galbraith Laboratories, Inc., Knoxville, Tenn. The analytical results for the elements indicated by there respective symbols were within ±0.4% of theoretical values. Optical rotations were measured with a Bellingham Stanley, Ltd., Model A polarimeter, type pl.

EXAMPLE 1

$\beta$-(S-Benzylmercapto)-$\beta$,$\beta$-cyclopentamethylenepropionyl-Tyr(Me)-Phe-Gln-Asn-Cys(Bzl)-Pro-Arg(Tos)-Gly-NH$_2$ (a) Combination of Solid Phase and Solution Methods Boc-Tyr(Me)-Phe-Gln-Asn-Cys(Bzl)-Pro-Arg(Tos)-Gly-NH$_2$, prepared by the method of Bankowski et al., *J. Med. Chem.*, vol. 21 (1978) at 850 (319 mg, 0.26 mmol), was dissolved in TEA (6.5 ml) and stirred at room temperature for 40 mins. Cold ether (20 ml) was added to produce a precipitate which was filtered and washed with ether (5×10 ml). The product was dried in vacuo over sodium hydroxide pellets. This material (318.5 mg) was dissolved in DMF (0.8 ml), to which was added N-methylmorpholine (10 $\mu$l). The resulting solution had a pH of 7-8, measured with moist pH paper. After this neutralized solution was stirred at room temperature for 30 min, a solution of p-nitrophenyl $\beta$-(S-benzyl-mercapto)-$\beta$,$\beta$-cyclopentamethylenepropionate, Nestor et al., *J. Med. Chem.* vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture still contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4×10 ml) and dried in vacuo. The crude product (339 mg) was twice reprecipitated from DMF-methanol to give the acylpeptide amide (295.2 mg, 77.3%): mp. 209°–211° C.; $[\alpha]_D^{24}=-43.6°$ (C 0.5, DMF); $R_f$(E) 0.45, $R_f$(F) 0.63 Anal. ($C_{73}H_{94}O_{14}N_{14}S_3$) C, H, N.

Amino acid analysis: Tyr, 0.80; Phe, 1.01; Glu, 1.04; Asp, 1.02; Cys(Bzl), 0.98; Pro, 1.06; Arg, 1.01; Gly, 1.00; NH$_3$ 2.91.

(b) Total Synthesis on Resin

Boc-Tyr(Me)-Phe-Gln-Asn-Cys(Bzl)-Pro-Arg(Tos)-Gly-resin (1.11 g, 0.4 mmol prepared from Boc-Gly-resin using solid phase methodology) was converted to the acyloctapeptide resin (1.167 g, weight gain 57 mg, 97.6% of theory) in one cycle of deprotection, neutralization and coupling with p-nitrophenyl $\beta$-(S-benzylmercapto)-$\beta$,$\beta$-cyclopentamethylenepropionate, see Nestor supra. The resin was ammonolyzed, Manning, *J. Am. Chem. Soc.*, vol. 90 (1968) at 1348. The product was extracted with dimethylformamide (DMF). After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp. 206°–208° C. (decomp); $R_f$(E), 0.45, $R_f$(F) 0.63; $[\alpha]_D^{24}=-43.1°$ (C 1, DMF). Anal. ($C_{73}H_{94}N_{14}O_{14}S_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly 1.00; $NH_3$, 2.95.

EXAMPLE 2

β-(S-Benzylmercapto)-β,β-cyclopentamethylenepropionyl-Tyr(Bzl)-Phe-Gln-Asn-Cys(Bzl)-Pro-Arg(Tos)-Gly-$NH_2$ Boc-Tyr(Bzl)-Phe-Gln-Asn-Cys(Bzl)-Pro-Arg(Tos)Gly-resin (1.46 g, 0.5 mmol) was converted to the acyloctapeptide resin (1.55 g, weight gain 70 mg, 95.9% of theory) as in Example 1 by one cycle of deprotection, neutralization and coupling with p-nitrophenyl β-(S-benzylmercapto)-β,β-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. (488 mg; 62.4% based on initial Gly content on the resin); mp. 183°–185° C.; $R_f(E)$ 0.38; $R_f(D)$ 0.41; $[\alpha]_D^{23} = -32.9°$ (C 1 DMF). Anal. ($C_{79}H_{98}N_{14}O_{14}S_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; $NH_3$.

EXAMPLE 3

[1-(β-Mercapto-β,β-cyclopentamethylenepropionic acid), 2-(O-methyl)tyrosine]arginine vasopressin (a) From Nonapeptide Amide A solution of the protected nonapeptide amide, prepared as in Example 1, (170 mg, 0.114 mmol) in 400 ml of ammonia (dried over sodium and redistilled) was stirred at the boiling point with sodium from a stick of the metal contained in a small bore glass tube until a light blue color persisted in the solution for 30 sec, in accordance with duVigneaud, J. Am. Chem. Soc., vol. 76 (1954) at 3115. Dry glacial acetic acid (0.4 ml) was added to discharge the color. The solution was evaporated. A solution of the residue in aqueous acetic acid (0.2%; 800 ml), was treated with 2 M ammonium hydroxide solution to give a solution of pH 7.5. To this stirred solution was added gradually an excess of a solution of potassium ferricyanide (0.01 M, 11.4 ml), Hope et al., J. Biol. Chem., vol. 237 (1962) at 1563. The yellow solution was stirred for 90 min more and for 1 h with anion-exchange resin (BioRad AG-3, Cl⁻form, 10 g damp weight). The suspension was filtered slowly through a bed of resin (80 g damp weight). The resin bed was washed with 300 ml of aqueous 0.2% acetic acid and the combined filtrate and washings were lyophylized. The resulting powder (1386 mg) was desalted on a Sephadex G-15 column (110×2.7 cm) and eluted with aqueous acetic acid (50%) at a flow rate of 4 ml/h by the technique of Manning et al., J. Chromatog., vol. 38 (1968) at 396. The eluate was fractioned and monitored for absorbance of 280 nm. The fractions comprising the major peak were pooled and lyophylized. The residue (55.5 mg) was further subjected to gel filtration on a Sephadex G-15 column (100×1.5 cm) and eluted with aqueous acetic acid (0.2 M) at a flow rate of 2.5 ml/h. The peptide was eluted in a single peak (absorbance 280 nm). Lyophilization of the pertinent fractions yielded the vasopressin analog (49 mg, 37.3%) $R_f(E)$ 0.19; $R_f(F)$ 0.30; $[\alpha]_D^{22} - 59.6$ (c0.19, 1 M AcOH).

Amino acid analysis: Tyr, 0.81; Phe 1.01; Glu, 1.04; Asp, 0.98; Pro, 1.04; Arg, 0.95; Gly, 1.00; $NH_3$, 3.10. Analysis following performic acid oxidation prior to hydrolysis according to Moore, J. Biol. Chem., vol. 238 (1963) at 235, gave a Cys($O_3H$)-Gly ratio of 1.03:1.00.

(b) From Acyloctapeptide

Treatment of the acyloctapeptide (160 mg, 0.107 mmol) as described in Example 3 (a) yielded the analog (64 mg, 51.7%), which was indistinguishable from the foregoing preparation by TLC: $[\alpha]_D^{23} - 59.1°$ (C 0.5, 1 M AcOH).

Amino acid analysis: Tyr, 0.80; Phe, 1.02; Glu, 1.02; Asp, 0.98; Pro, 1.03; Arg, 0.96; Gly, 1.00; $NH_3$, 3.05. Analysis following performic acid oxidation prior to hydrolysis gave a Cys($O_3H$)-Gly ratio of 1.02:1.00.

EXAMPLE 4

[1-(β-Mercapto-β,β-cyclopentamethylenepropionic acid)]arginine vasopressin

Treatment of the acyloctapeptide (173 mg, 0.111 mmol) as described in Example 3 (a) yielded the analog (66 mg, 52.5%) $R_f(E)$ 0.19, $R_f(F)$ 0.43. $[\alpha]_D^{23} - 58.7°$ (C 0.5, 1 M AcOH).

Amino acid analysis: Tyr, 0.96; Phe, 0.98; Glu, 1.01; Asp, 1.01; Pro, 1.05; Gly, 1.00; $NH_3$, 2.95. Analysis following performic acid oxidation prior to hydrolysis gave a Cys($O_3H$)-Gly ratio of 1.01:1.00.

EXAMPLE 5

[1-(β-Mercapto-β,β-cyclopentamethylenepropionic acid), 2-(O-alkyl)tyrosine, 4-valine]-(L- and D-)-arginine vasopressin Compounds of this series were prepared by solid-phase synthesis, modified as in Manning et al., J. Med. Chem., vol. 16 (1973) at 975 and Kruszynski et al., J. Med. Chem., vol. 23 (1980) at 364, to obtain protected intermediates for each analog. The procedures of Bodanszky et al., J. Am. Chem. Soc., vol. 81 (1959) at 5688 and J. Org. Chem., vol. 39 (1974) at 444, employing a p-nitrophenyl ester, facilitated by the use of hydroxybenzotriazole (Konig et al., supra), were used for the coupling of β-(S-benzylmercapto-β,β-cyclopentamethylenepropionic acid in accordance with Nestor, supra, to obtain precursor compounds. Each precursor was deblocked (duVigneaud, supra) with sodium in liquid ammonia. The resulting disulfhydryl compounds were oxidatively cyclized with potassium ferricyanide (Hope et al., supra). The analogs were desalted and purified by gel filtration on Sephadex G-15 by a two step procedure using 50% acetic acid and 0.2 M acetic acid, respectively, as eluants. The purity and identity of each analog was ascertained by thin-layer chromatography in three different solvent systems, Kruszynski et al., J. Med. Chem., vol. 23 (1980) at 364, and by amino acid analysis as above.

Boc-Phe-Val-Asn-Cys(Bzl)-Pro-D-Arg(Tos)-Gly-resin

Boc-Gly-resin (1.562 g, 1.0 mmol, of Gly) was subjected to six cycles of deprotection, neutralization, and coupling to yield the protected heptapeptidyl resin A (2.522 g, 1.0 mmol).

Boc-Phe-Val-Asn-Cys(Bzl)-Pro-Arg(Tos)-Gly-resin

The protected heptapeptidyl resin B (2.522 g, 1.0 mmol) was prepared from 1.562 g (1.0 mmol) of Boc-Gly-resin using solid-phase methodology.

Boc-Tyr(Me)-Phe-Val-Asn-Cys(Bzl)-Pro-D-Arg(Tos)-Gly-resin

A single cycle of solid-phase peptide synthesis with Boc-Tyr(Me) as the carboxy component converted heptapeptidyl resin A (1.261 g, 0.5 mmol) to the corresponding tert-butyloxycarbonyloctapeptidyl resin C (1.35 g, 0.5 mmol).

Boc-Tyr(Et)-Phe-Val-Asn-Cys(Bzl)-Pro-D-Arg(Tos)-Gly-resin

The heptapeptidyl resin A (1.261 g, 0.5 mmol) yielded the tert-butyloxycarbonyloctapeptidyl resin D (1.357 g, 0.5 mmol) in one cycle of solid-phase peptide synthesis with Boc-Tyr(Et) as the carboxy component.

Boc-Tyr(Me)-Phe-Val-Asn-Cys(Bzl)-Pro-Arg(Tos)-Gly-resin

The heptapeptidyl resin B (1.261 g, 0.5 mmol) was converted to protected octapeptidyl resin E (1.35 g, 0.5 mmol) in one cycle of deprotection, neutralization and coupling with Boc-Tyr(Me).

β-(S-Benzylmercapto)-β,β-cyclopentamethylene-propiony-Tyr(Et)-Phe-Val-Asn-Cys(Bzl)-Pro-Arg(Tos)-Gly-resin The heptapeptidyl resin B (1.261 g, 0.5 mmol) was converted to the acyloctapeptide resin (1.43 g, 0.5 mmol) in two cycles of solid phase peptide synthesis using as the carboxy component, respectively: Boc-Tyr(Et) and p-nitrophenyl β-(S-benzylmercapto)-β,β-cyclopentamethylenpropionate.

Boc-Tyr(Me)-Phe-Val-Asn-Cys(Bzl)-Pro-D-Arg(Tos)-Gly-NH₂

The protected octapeptide resin C (1.35 g, 0.5 mmol) was ammonolyzed and the product extracted with warm DMF. The product was precipitated by addition of water. The crude product was reprecipitated from DMF-ethanol-ethyl ether to give the pure product as a white powder (0.581 g, 88.52% based on initial Gly content of the resin) mp. 239°–240° C.; $[\alpha]_D^{24} = -14.9°$ (C=1, DMF); $R_f(E)$, 0.54, $R_f(D)$, 0.73; Anal. ($C_{63}H_{85}N_{13}O_{14}S_2$) C, H, N.

Amino acid analysis: Tyr, 1.02; Phe, 0.98; Val, 1.02; Asp, 1.00; Cys(Bzl), 0.98; Pro, 1.01; Arg, 0.97; Gly, 1.00; NH₃, 2.1.

Boc-Tyr(Et)-Phe-Val-Asn-Cys(Bzl)-Pro-D-Arg(Tos)-Gly-NH₂

Treatment of the protected octapeptide resin D (1.357 g, 0.5 mmol) as above yielded the Boc-octapeptideamide (0.535 g, 80.69% based on initial Gly content of the resin) mp. 211°–213° C.; $[\alpha]_D^{24} = -16.4°$ (C=1, DMF); $R_f(E)$, 0.61, $R_f(D)$, 0.83; Anal. ($C_{64}H_{87}N_{13}O_{14}S_2$) C, H, N.

Amino acid analysis: Tyr, 0.99; Phe, 1.00; Val, 1.01; Asp, 1.02; Cys(Bzl), 0.98; Pro, 1.00; Arg, 0.98; Gly, 1.00; NH₃, 2.13.

Boc-Tyr(Me)-Phe-Val-Asn-Cys(Bzl)-Pro-Arg(Tos)-Gly-NH₂

Treatment of the protected octapeptide resin E (1.35 g, 0.5 mmol) as above gave the corresponding Boc-octapeptideamide (0.597 g, 90.96% based on initial Gly content of the resin). mp. 216°–217° C. (decomp.); $[\alpha]_D^{24} = -34.82°$ (C=1, DMF); $R_f(E)$, 0.54, $R_f(D)$, 0.73; Anal. ($C_{63}H_{85}N_{13}O_{14}S_2$) C, H, N.

Amino acid analysis: Tyr, 0.99; Phe, 1.00; Val, 1.02; Asp, 1.01; Cys(Bzl), 0.98; Pro, 1.01, Arg, 0.98; Gly, 1.00; NH₃, 2.09.

β-(S-Benzylmercapto-β,β-cyclopentamethylenepropionyl-Tyr(Et)-Phe-Val-Asn-Cys(Bzl)-Pro-Arg(Tos)-Gly-NH₂

The protected acyloctapeptide resin (1.43 g, 0.5 mmol) was ammonolyzed and the product extracted with warm DMF. The product was precipitated by addition of water. The crude product was reprecipitated from DMF-ethanol-ethyl ether to give the pure product. (0.490 g, 66.54% based on initial Gly content of the resin). mp. 211°–213° C.; $[\alpha]_D^{24} = -39.8°$ (C=1, DMF); $R_f(E)$, 0.59, $R_f(D)$, 0.75; Anal. ($C_{74}H_{97}N_{13}O_{13}S_3$) C, H, N.

Amino acid analysis: Tyr, 0.99; Phe, 1.01; Val, 1.01; Asp, 1.01; Cys(Bzl), 0.99; Pro, 1.02; Arg, 0.98; Gly, 1.00; NH₃, 2.07.

β-(S-Benzylmercapto)-β,β-cyclopentamethylenepropionyl-Tyr(Me)-Phe-Val-Asn-Cys(Bzl)-Pro-D-Arg(Tos)Gly-NH₂

The tert-butyloxycarbonyloctapeptide amide prepared above (0.270 g, 0.206 mmol), was dissolved in TFA (3 ml) and allowed to stand at room temperature for 20 min. Cold ether was added. The precipitated material was filtered and washed with ether (5 × 10 ml). The product was dried in vacuo over sodium hydroxide pellets. This material (250 mg) was dissolved in DMF (0.8 ml) to which solution N-methylmorpholine was added to give a solution of pH 7–8 (moist pH paper). The neutralized solution was stirred at room temperature for 20 min. A solution of p-nitrophenyl β-(S-benzylmercapto-β,β-cyclopentamethylenepropionate (0.135 g, 0.37 mmol) and N-hydroxybenzotriazole monohydrate (57 mg, 0.37 mmol) in DMF (1.0 ml) was added. The reaction mixture was stirred at room temperature overnight and TLC (system E) showed that the reaction was complete. Methanol (80 ml) and ether (20 ml) were added with vigorous mixing. The precipitated material was filtered, washed with a mixture of methanol-ether (8:2), and dired in vacuo. The crude product (270 mg) was reprecipitated form DMF-methanol to give the acyl peptide amide (263 mg, 75.2%); mp. 220°–221° C.; $[\alpha]_D^{24} = -25.7°$ (C=1, DMF); $R_f(E)$, 0.55, $R_f(D)$, 0.83; Anal. ($C_{73}H_{95}N_{13}O_{13}S_3$) C, H, N.

Amino acid analysis: Tyr, 0.98; Phe, 1.01; Val, 1.02; Asp, 1.02; Cys(Bzl), 0.97; Pro, 1.03; Arg, 1.0; Gly, 1.00; NH₃, 2.06.

β-(S-Benzylmercapto-β,β-cyclopentamethylenepropionyl-Tyr(Et)-Phe-Val-Asn-Cys(Bzl)-Pro-D-Arg(Tos)-Gly-NH₂

The tert-butyloxycarbonyloctapeptide amide (0.398 g, 0.3 mmol) was deprotected and coupled with p-nitrophenyl β-(S-benzylmercapto)-β,β-cyclopentamethylenepropionate (0.232 g, 0.6 mmol) as described above to give the acyloctapeptide amide (0.361 g, 81.67%) mp. 222°–224° C.; $[\alpha]_D^{20} = -22.8°$ (C=0.5, DMF); $R_f(E)$, 0.5, $R_f(D)$, 0.83; Anal. ($C_{74}H_{97}N_{13}O_{13}S_3$) C, H, N.

Amino acid analysis: Tyr, 1.0; Phe, 1.02; Val, 1.03; Asp, 1.02; Cys(Bzl), 0.98; Pro, 1.03; Arg, 0.99; Gly, 1.00; NH$_3$, 2.11.

β-(S-Benzylmercapto)-β,β-cyclopentamethylenepropionyl-Tyr(Me)-Phe-Val-Asn-Cys(Bzl)-Pro-Arg(Tos)-Gly-NH$_2$ Tert-Butyloxycarbonyloctapeptide amide (0.394 g, 0.3 mmol) was deprotected and coupled with p-nitrophenyl β-(S-benzylmercapto)-β,β-cyclopentamethylenepropionate (0.232 g, 0.6 mmol) as above to produce the acyloctapeptide amide (0.388 g, 88.65%); mp. 211°–214° C.; $[\alpha]_D^{21} = -39.2°$ (C=1, DMF); R$_f$(E), 0.47, R$_f$(D), 0.85; Anal. (C$_{73}$H$_{95}$N$_{13}$O$_{13}$S$_3$) C, H, N.

Amino acid analysis: Tyr, 0.99; Phe, 1.02; Val, 1.03; Asp, 1.01; Cys(Bzl), 0.99; Pro, 1.02; Arg, 0.99; Gly, 1.00; NH$_3$, 2.04.

[1-(β-Mercapto-β,β-cyclopentamethylenepropionic acid), 2-(O-ethyl)tyrosine, 4-valine]-arginine vasopressin A solution of protected acylocta-peptide amide (140 mg, 0.095 mmol) in 400 ml of ammonia (dried and redistilled from sodium) was stirred and treated at the boiling point with sodium from a stick of the metal contained in a small-bore glass tube until a light blue color persisted in the solution for 30 s. Dry glacial acetic acid (0.4 ml) was added to discharge the color. The solution was evaporated by passing N$_2$ through the flask. After 5 min, the residue was dissolved in aqueous acetic acid (10%, 50 ml) to which was added 800 ml of water. The solution was treated with 2 M ammonium hydroxide solution to give a solution of pH-6.5. An excess of a solution of potassium ferricyanide (0.01 M, 16 ml) was added gradually with stirring. The yellow solution was stirred for 10 min more and for 10 min with anion exchange resin (Bio-Rad-AG-3, Cl$^-$ form, 10 g damp weight). The suspension was slowly filtered through a bed of resin (50 g damp weight). After washing the bed with aqueous acetic acid (0.2%, 200 ml), the combined filtrate and washings were lyophylized. The resulting powder (1.63 g) was desalted on a Sephadex G-15 column (110×2.7 cm) by elution with aqueous acetic acid (50%) at a flow rate 5 ml/h. The eluate was fractionated and monitored for absorbance of 280 nm. The fractions comprising the major peak were pooled and lyophylized. The residue (28 mg) was subjected to gel filtration on a Sephadex G-15 column (100×1.5 cm). Product was eluted with aqueous acetic acid (0.2 M) at a flow rate of 4 ml/h. The peptide was eluted in a single peak (absorbance 280 nm). Lyophylization of the pertinent fractions yielded the vasopressin analog (24 mg, 20.6%). TLC R$_f$(E), 0.31, R$_f$(F), 0.62; $[\alpha]_D = -65.1°$ (C=0.2, 1 M AcOH).

Amino acid analysis: Tyr, 1.00; Phe, 1.01; Val, 1.01, Aps, 1.01; Pro, 1.01; Arg, 1.00; Gly, 1.00; NH$_3$, 1.97. Analysis following performic acid oxidation prior to hydrolysis gave a Cys(O$_3$H)-Gly ratio of 1.01:1.00.

[1-(β-Mercapto-β,β-cyclopentamethylenepropionic acid), 2-(O-methyl)tyrosine, 4-valine, 8-D-arginine] vasopressin The peptide intermediate (168 mg, 0.115 mmol) was reduced by sodium in liquid ammonia, reoxidized, deionized, and purified as above to give 49.5 mg of product (35.5%) R$_f$(E), 0.30, R$_f$(F), 0.61; $[\alpha]_D^{23} = -46.4°$ (C=0.4, 1 M AcOH).

Amino acid analysis: Tyr, 0.98; Phe, 1.01; Val, 0.98; Asp, 0.99; Pro, 1.03; Arg, 0.98; Gly, 1.00; NH$_3$, 12.1. Analysis following performic acid oxidation prior to hydrolysis gave a Cys(O$_3$H)-Gly ratio 1.03:1.00.

[1-(β-Mercapto-β,β-cyclopentamethylenepropionic acid), 2-(O-ethyl)tyrosine, 4 valine, 8-D-arginine] vasopressin The yield of analog from 167 mg (0.113 mmol) of intermediate was 29 mg (20.9%). R$_f$(E), 0.29, R$_f$(F), 0.57; $[\alpha]_D^{23} = -41.1°$ (C=0.3, 1 M AcOH).

Amino acid analysis: Tyr, 0.98; Phe, 1.01; Val, 1.03; Asp, 0.99; Pro, 1.03; Arg, 1.02; Gly, 1.00; NH$_3$, 1.98. Analysis following performic acid oxidation prior to hydrolysis gave a Cys(O$_3$H)-Gly ratio 1.01:1.00.

[1-(β-Mercapto-β,β-cyclopentamethylenepropionic acid), 2-(O-methyl)tyrosine, 4-valine]-arginine vasopressin Treatment of the acyl octapeptide (174 mg, 0.119 mmol) as above yielded the 51.5 mg of product (35.6%). R$_f$(E), 0.28, R$_f$(F), 0.60; $[\alpha]_D^{23} = -66.3°$ (C=0.4, 1 M AcOH).

Amino acid analysis: Tyr, 0.99; Phe, 1.01; Val, 1.02; Asp, 1.01; Pro, 1.00; Arg, 1.01; Gly, 1.00; NH$_3$, 2.11. Analysis following performic acid oxidation prior to hydrolysis gave a Cys(O$_3$H)-Gly ratio 1.03:1.00.

EXAMPLE 6

[1-(β-Mercapto-β,β-cyclopentamethylenepropionic acid), 2-(O-ethyl)tyrosine, 4-valine, 7-(3,4-dehydroproline)] arginine vasopressin The compound was prepared as in Example 5, using Δ$^3$-proline instead of proline.

EXAMPLE 7

Antagonism to the vasopressor response to AVP was estimated in accordance with Dyckes et al., *J. Med. Chem.*, vol. 17 (1974) at 969. The values are expressed as pA$_2$ values, defined by Schild et al., *Br. J. Pharmacol.*, vol. 2 (1947) at 189.

Activity as antidiuretic agonists was determined by intravenous injection of compounds being evaluated into ethanol-anesthesized water-loaded rats in accordance with Sawyer et al., *Endocrinology*, vol. 63 (1958) at 694.

Results displayed in Table I show that compounds of this invention, particularly [1-(β-mercapto-β,β-cyclopentamethylenepropionic acid), 8-arginine] vasopressin and [1-(β-mercapto-β,β-cyclopentamethylenepropionic acid), 2-(O-methyl)tyrosone, 8-arginine] vasopressin antagonize the vasopressor response to arginine vasopressin and also exhibit a marked reduction in antidiuretic activity.

TABLE I $$\begin{array}{c} \overset{1}{CH_2}-CO-\overset{2}{X^1}-\overset{3}{Phe}-\overset{4}{Y}-\overset{5}{Asn}-\overset{6}{Cy}-\overset{7}{Pro}-\overset{8}{Z}-\overset{9}{Gly}-NH_2 \\ | \qquad\qquad\qquad\qquad\qquad\qquad | \\ R-C-R \qquad\qquad\qquad\qquad\qquad\quad | \\ | \qquad\qquad\qquad\qquad\qquad\qquad | \\ S------------S \end{array}$$

| Peptide | $R_2$ | $X^1$ | Y | Z | Antivasopressor $pA_2$ | Antidiuretic U/mg |
|---|---|---|---|---|---|---|
| dAVP | $(H)_2$ | Tyr | Gln | Arg | Agonist | 1745 ± 385 |
| dPAVP | $(CH_3)_2$ | Tyr | Gln | Arg | 7.45 ± 0.11 | 42 ± 3 |
| d(CH$_2$)$_5$AVP | $(CH_2)_5$ | Tyr | Gln | Arg | 8.35 ± 0.99 | 0.033 ± 0.005 |
| dVDAVP | $(H)_2$ | Tyr | Val | D-Arg | 7.03 ± 0.11 | 1230 ± 170 |
| dPVDAVP | $(CH_3)_2$ | Tyr | Val | D-Arg | 7.82 ± 0.05 | 123 ± 22 |
| d(CH$_2$)$_5$VDAVP | $(CH_2)_5$ | Tyr | Val | D-Arg | 7.68 ± 0.05 | 0.10 ± 0.02 |
| dTyr(Me)AVP | $H_2$ | Tyr(Me) | Gln | Arg | Agonist | 830 ± 70 |
| dPTyr(Me)AVP | $(CH_3)_2$ | Tyr(Me) | Gln | Arg | 7.96 ± 0.05 | 3.5 ± 0.5 |
| d(CH$_2$)$_5$Tyr(Me)AVP | $(CH_2)_5$ | Tyr(Me) | Gln | Arg | 8.62 ± 0.03 | 0.31 ± 0.07 |

EXAMPLE 8

[1-($\beta$-Mercapto-$\beta$,$\beta$-cyclopentamethylenepropionic acid), 2-(O-alkyl)tyrosine, 4-valine, 8-(L- and D-) arginine] vasopressin compounds, evaluated as in Example 6, were weak antidiuretic agonists. They caused an initial submaximal inhibition of urine flow lasting about 10 min, followed by a period of inhibition of responses to ADH lasting 1 to 3 h, depending on the dose. This inhibition was reversible, that is, could be overcome by raising the dose of ADH. Repeated assays permitted estimation of the "effective dose" of each analog, which is defined as the dose which reduces the antidiuretic response to 2x units of ADH injected 20 min after the dose of antagonist to equal the response to 1x units injected prior to the antagonist. The estimated effective doses for these analogs were (in nmoles/kg):

| Compound | Effective dose |
|---|---|
| d(CH$_2$)$_5$Tyr(Me)VDAVP | 15 ± 3 |
| d(CH$_2$)$_5$Tyr(Et)VDAVP | 5.7 ± 0.5 |
| d(CH$_2$)$_5$Tyr(i-Pr)VDAVP | 8.5 ± 1.7 |
| d(CH$_2$)$_5$Tyr(n-Pr)VDAVP | 17 ± 2 |
| d(CH$_2$)$_5$Tyr(Me)VAVP | 3.1 ± 0.4 |
| d(CH$_2$)$_5$—D-Tyr(Me)VAVP | 1.2 ± 0.3 |
| d(CH$_2$)$_5$Ytr(Et)VAVP | 1.9 ± 0.2 |
| d(CH$_2$)$_5$Tyr(i-Pr)VAVP | 3.6 ± 0.9 |
| d(CH$_2$)$_5$Tyr(n-Pr)VAVP | 3.5 ± 0.6 |
| d(CH$_2$)$_5$Tyr(Et)V$\Delta^3$Pro$^7$—AVP | 1.6 ± 0.3 |

EXAMPLE 9

(a) Antagonism of [1-($\beta$-mercapto-$\beta$,$\beta$-cyclopentamethylenepropionic acid), 2-(O-alkyl)tyrosine, 4-valine]-(L- and D-)-arginine vasopressin compounds to endogenous ADH was shown by injection of the compound intraperitoneally into conscious rats. Urine was collected for 4 h after the injections. The data in the Table below are the means ± SE of results on groups of 4–6 rats. *P<0.05 and **P<0.005 are given for differences between the means for rats receiving antagonists and the means for responses of the same rats injected with solvent only. The mean control urine volume rate for solvent-injected rats was 0.9±0.1 ml/kg per hr and the mean osmolality was 1544±85 mOsm/kg H$_2$O (n=32).

| | Dose ug/kg | Urine volume ml/kg per hr | Osmolality mOsm/kg H$_2$O |
|---|---|---|---|
| d(CH$_2$)$_5$Tyr(Me)-VDAVP | 100 | 1.5 ± 0.3 | 1341 ± 428 |
| | 300 | 2.2 ± 0.4* | 961 ± 204** |
| d(CH$_2$)$_5$Tyr(Et)-VDAVP | 30 | 2.8 ± 0.3** | 640 ± 47** |
| | 100 | 9.5 ± 1.8** | 234 ± 25** |
| d(CH$_2$)$_5$Tyr(Me)-VAVP | 10 | 1.1 ± 0.5 | 1303 ± 190 |
| | 30 | 3.4 ± 0.9* | 514 ± 105** |
| d(CH$_2$)$_5$Tyr(Et)-VAVP | 10 | 7.4 ± 1.0** | 316 ± 38** |
| | 30 | 13.3 ± 2.5** | 194 ± 17** |

(b) Responses by intact female rats, weighing 200 to 240 g, to intraperitoneal injections of d(CH$_2$)$_5$Tyr(Et)-VAVP was determined in a block design experiment in which each rat received solvent and both doses of the ADH antagonist. Injections were given at least two days apart. The rats were on water ad lib. Injections were made at 11 a.m., after which spontaneously voided urine was collected hourly for four hours.

Figure 1:
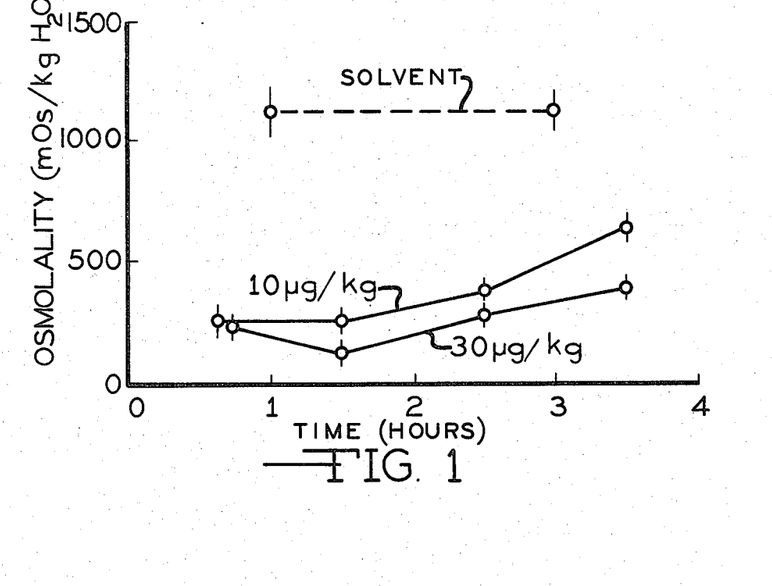
In FIG. 1 are shown urine osmolalities, as a function of time, of rats treated intraperitoneally with a compound of this invention.

In FIG. 1 is shown osmolality of the urine as a function of time. Urine osmolalities for the control (solvent-injected) were averaged over 2 hour periods owing to infrequency of urination.

Figure 2:
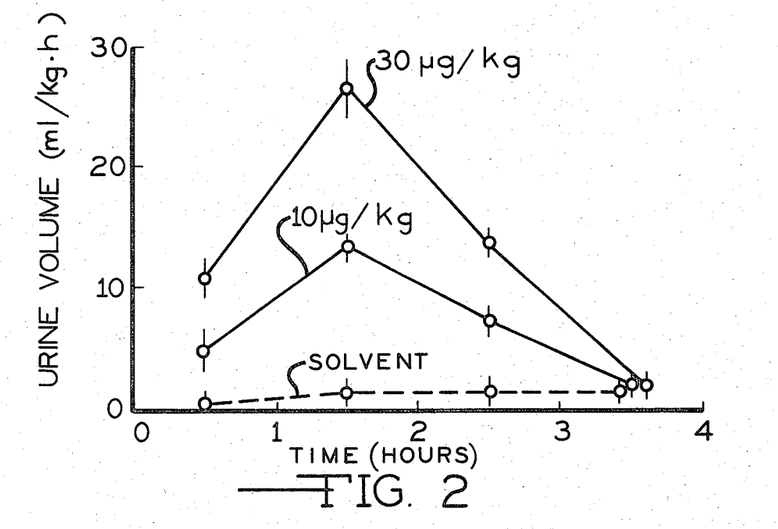
In FIG. 2 is shown urine output, as a function of time, of rats treated with a compound of this invention.

In FIG. 2 is shown the urine output as a function of time.

In both Figures, vertical lines through points indicate SE's.

EXAMPLE 10

Compounds otherwise of Formula I, but wherein the amino acid at the 2 position is unetherified D-Tyr (X is H), are prepared as in Examples 1–5. The compound in which Z- is L-Arg is very active as an antagonist of the antidiuretic activity of arginine vasopressin.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of the formula wherein X is methyl, ethyl, n-propyl, isopropyl or butyl; Try is L- or D-; W is Pro or Δ³-Pro; and Z is L- or D-Arg.

2. [1-(β-Mercapto-β,β-cyclopentamethylenepropionic acid), 2-(O-methyl)tyrosine, 4-valine, 8-arginine] vasopressin, a compound of claim 1.

3. [1-(β-Mercapto-β,β-cyclopentamethylenepropionic acid), 2-(O-methyl)tyrosine, 4-valine, 8-(L- or D-) arginine] vasopressin, a compound of claim 1.

4. [1-(β-Mercapto-β,β-cyclopentamethylenepropionic acid), 2-(O-ethyl)tyrosine, 4-valine, 8-(L- or D-) arginine] vasopressin, a compound of claim 1.

5. [1-(β-Mercapto-β,β-cyclopentamethylenepropionic acid), 2-(O-methyl)-D-tyrosine, 4-valine, 8-(L- or D-) arginine] vasopressin, a compound of claim 1.

6. [1-(β-Mercapto-β,β-cyclopentamethylenepropionic acid), 2-(O-isopropyl)tyrosine, 4-valine, 8-(L- or D-) arginine] vasopressin, a compound of claim 1.

7. [1-(β-Mercapto-β,β-cyclopentamethylenepropionic acid), 2-(O-n-propyl)tyrosine, 4-valine, 8-(L- or D-) arginine] vasopressin, a compound of claim 1.

8. [1-(β-Mercapto-β,β-cyclopentamethylenepropionic acid), 2-(O-ethyl)tyrosine, 4-valine, 7-(3,4-dehydroproline)] arginine vasopressin, a compound of claim 1.

9. A method for antagonizing the in vivo response of an animal to the antidiuretic action of an antidiuretic hormone, comprising administering to the animal being treated an amount of a compound of claim 1, in admixture with a physiologically and pharmaceutically acceptable carrier, effective to antagonize the antidiuretic response to the antidiuretic hormone.

10. The method of claim 9, wherein the antidiuretic hormone is arginine vasopressin.

11. The method of claim 9, wherein the compound is administered parenterally.

12. A method for antagonizing the in vivo response of an animal to the antidiuretic action of an antidiuretic hormone, comprising administering to the animal being treated an amount of the compound of claim 5, in admixture with a physiologically and pharmaceutically acceptable carrier, effective to antagonize the antidiuretic response to the antidiuretic hormone.

13. A method for antagonizing the in vivo response of an animal to the antidiuretic action of an antidiuretic hormone, comprising administering to the animal being treated an amount of the compound of claim 8, in admixture with a physiologically and pharmaceutically acceptable carrier, effective to antagonize the antidiuretic response to the antidiuretic hormone.

14. A compound of the formula wherein X is H, methyl or ethyl and Z is L- or D-Arg.
wherein X is H, methyl and Z is L- or D-Arg.

15. A method for antagonizing the in vivo vasopressor response of an animal to a vasopressor hormone comprising administering to the animal being treated an amount of a compound of claim 14, in admixture with a physiologically and pharmaceutically acceptable carrier, effective to antagonize the vasopressor response to the vasopressor hormone.

16. The method of claim 15, wherein the vasopressor hormone is arginine vasopressin.

17. A compound of the formula wherein Tyr is D-Tyr and Z- is D- or L-Arg.

* * * * *